US009279785B2

(12) United States Patent
Zhang

(10) Patent No.: US 9,279,785 B2
(45) Date of Patent: Mar. 8, 2016

(54) MONITORING TEMPERATURE VARIATION IN WEDGE OF PHASED-ARRAY PROBE FOR WELD INSPECTION

(71) Applicant: Jinchi Zhang, Québec (CA)

(72) Inventor: Jinchi Zhang, Québec (CA)

(73) Assignee: OLYMPUS NDT, Waltham, MA (US)

( * ) Notice: Subject to any disclaimer, the term of this patent is extended or adjusted under 35 U.S.C. 154(b) by 307 days.

(21) Appl. No.: 13/907,063

(22) Filed: May 31, 2013

(65) Prior Publication Data

US 2014/0352436 A1 Dec. 4, 2014

(51) Int. Cl.
*G01N 29/07* (2006.01)
*G01N 29/04* (2006.01)
*G01N 29/26* (2006.01)
*G01N 29/28* (2006.01)
*G01N 29/32* (2006.01)

(52) U.S. Cl.
CPC .............. *G01N 29/07* (2013.01); *G01N 29/262* (2013.01); *G01N 29/28* (2013.01); *G01N 29/326* (2013.01); *G01N 2291/017* (2013.01); *G01N 2291/2675* (2013.01)

(58) Field of Classification Search
CPC .............. G01N 29/07; G01N 29/0681; G01N 29/2418; G01N 29/2437; G01N 29/223; G01N 29/2487; G01N 29/26; G01N 29/06; G01N 29/24; G01N 2291/017; G01N 2291/2675; G01N 29/262; G01N 29/28; G01N 29/326
USPC ............................................. 73/596, 597, 598
See application file for complete search history.

(56) References Cited

U.S. PATENT DOCUMENTS

| | | | | |
|---|---|---|---|---|
| 3,554,013 A * | 1/1971 | Berg | ............... | 73/609 |
| 4,020,679 A * | 5/1977 | Barry | ............... | 73/644 |
| 4,143,554 A * | 3/1979 | Nagy et al. | ............... | 73/641 |
| 4,153,894 A * | 5/1979 | Alphonse et al. | ............... | 367/7 |
| 4,195,530 A * | 4/1980 | Ross et al. | ............... | 73/638 |
| 4,398,421 A * | 8/1983 | White | ............... | 73/597 |
| 4,437,332 A * | 3/1984 | Pittaro | ............... | 73/597 |
| 4,467,659 A * | 8/1984 | Baumoel | ............... | 73/861.27 |
| 4,712,428 A * | 12/1987 | Ishii et al. | ............... | 73/644 |
| 5,913,243 A * | 6/1999 | Hopeck et al. | ............... | 73/644 |
| 6,332,361 B1 * | 12/2001 | Yamada et al. | ............... | 73/627 |
| 8,210,046 B2 * | 7/2012 | Luo et al. | ............... | 73/644 |
| 8,302,480 B2 * | 11/2012 | Maris et al. | ............... | 73/643 |
| 2005/0139013 A1 * | 6/2005 | Hashimoto et al. | ............... | 73/861.27 |
| 2006/0065055 A1 * | 3/2006 | Barshinger et al. | ............... | 73/609 |
| 2009/0049918 A1 * | 2/2009 | Luo et al. | ............... | 73/627 |
| 2010/0250151 A1 * | 9/2010 | Rager et al. | ............... | 702/39 |
| 2011/0247417 A1 * | 10/2011 | Oberdoerfer et al. | ............... | 73/598 |

* cited by examiner

*Primary Examiner* — Helen Kwok
(74) *Attorney, Agent, or Firm* — Ostrolenk Faber LLP

(57) ABSTRACT

A coupling wedge for use with a ultrasonic phased array inspection system has a body with a bottom side configured to face the object to be tested and a front side generally oriented at an angle to the bottom side and a top side to be coupled with a phased array probe. The probe includes a plurality of apertures. The front side of the wedge has grooves formed with a plurality of reflectors that are positioned on the front side of the wedge, leaving a distance from the bottom side. The change in TOF values from the reflector to a specific aperture enable the determination of the temperature change in the wedge. An alarm to an operator or alternation of focal laws in the system for temperature compensation can be applied.

20 Claims, 7 Drawing Sheets

MONITORING TEMPERATURE VARIATION IN WEDGE OF PHASED-ARRAY PROBE FOR WELD INSPECTION

FIELD OF THE INVENTION

The present invention relates to a method and system for providing non-destructive inspection and testing (NDI/NDT), more particularly, to a method and system employing a search unit with a wedge and a phased-array probe and a phased array system with the capability of detecting temperature change in the wedge.

BACKGROUND OF THE INVENTION

It is an object of the present invention to provide a hot weld seam inspection system and method which detects, alerts and compensates for wedge temperature variations.

In many ultrasonic weld seam inspections with a contact mode, such as in girth weld inspections during pipeline construction, phased-array probes are used with wedges. The wedges are usually of a thermoplastic synthetic material, in particular, a cross-linked polystyrene copolymer, for example Rexolite. The wedge is placed on the part surface, e.g., pipe surface, in close proximity to the weld seam which may be still quite hot from the welding. The ultrasonic wave propagates between the wedge and the pipe surface through a liquid couplant, which in most cases is water supplied by a pump. To allow the water to flow evenly, the wedge bottom is spaced from the part surface at a small gap of about 0.1 mm. The small gap is maintained, for example, by using four anti-wearing pins screwed in the four corners of the wedge bottom to prevent it from contacting the surface. The pumped water flows through the small gap completely filling it, which enables the ultrasonic coupling.

For an inspection using a pulse-echo mode, which uses electrical pulses coming from an acquisition unit to produce excitations, ultrasonic beams of longitudinal waves (LW) generated by different apertures of the phased-array probe travel in the wedge, propagate through the small water-filled gap, penetrate into the part and then reach the weld zone. If there is a flaw in the weld zone, some ultrasonic beams may be reflected by the flaw and then return to the probe. The probe, operating as a receiver, senses the returned ultrasonic beams and outputs the flaw echo signals to the acquisition unit for signal display.

When the ultrasonic beams travel through the interface at the wedge bottom surface, some of them skip back to the wedge front, potentially causing unwanted wedge echoes. To reduce the problem, damping material is casted to the wedge front, to absorb those unwanted echoes. The solidified damping material has an acoustic impedance very similar to that of the wedge material. To efficiently absorb and scatter the wedge echoes, grooves with serrated sections are machined in the wedge front. The grooves extend approximately perpendicularly to the plane of the probe face and are machined through the wedge front height. The larger the size of the serrations, the better the efficiency of the wedge echo attenuation. However, big serrations increase the distance from the exit points to the weld. A typical sectional shape of the grooves is an isosceles triangle with, for example, 3 mm side lengths.

In practice, an inspection of a newly welded seam involves the operator making sure that the pipe surface temperature is well below the water boiling temperature, i.e., 100° C. The temperature is typically measured with a non-contact infrared temperature gauge. A pipe or part surface at a higher temperature will boil the coupling water and generate bubbles that can seriously attenuate or even cut the ultrasonic wave propagation in the coupling water layer. Preferably, the part surface temperature suitable to weld inspection should be lower than 80° C.

The pumped water flowing around and under the wedge in the small gap serves not only as an ultrasonic wave couplant but also as a coolant that keeps the wedge temperature at that of the pumped water. In other words, normally the pumped water is a perfect coolant for the wedge. On rare occasions however, when, for example, the running water is interrupted or the wedge bottom contacts directly the hot part, the wedge temperature can be affected. Unlike metal parts such as a steel part, the longitudinal wave velocity in plastic wedge is much more sensitive to temperature changes. According to Snell's Law, a LW velocity change in a wedge can induce a change of the refraction angle of the inspection beams in the part, wrongly directing the beams in the part and possibly causing a total miss of the weld zones being inspected. The requirements for temperature condition in girth weld inspections can be found in Section 9.4.3 Temperature Differentials and Control, in Standard Practice for Mechanized Ultrasonic Examination of Girth Welds Using Zonal Discrimination with Focused Search Units, Designation: E 1961-98 (Reapproved 2003)$^{e1}$, ASTM International. What is even more complex is that, once the wedge is heated, the temperature field in it is normally a function of time, which makes compensation of the temperature change in the wedge by modifying the focal laws in real time very complex and difficult. Even if this method was feasible, it would be too expensive to provide it for the rare and accidental event of a wedge temperature change. Therefore the efficient way to counteract the temperature change in a wedge, is to monitor for temperature changes, and to record an alarm for the event. Then the operator can take measures to deal with the event and can continue the inspection after the temperature level in the wedge has been restored.

The following prior art addresses the subject of wedge temperature detection or wedge temperature real time compensation.

The General Electric pending patent publication US 2011/0247417 A1 discloses a method that uses wedge bottom as the reflector and use the variation of the time of flight (TOF) or the sound path from the PA probe to the wedge bottom as the indication of temperature change in wedge. The major drawback of the method is that the amplitude and TOF of the echoes from the wedge bottom can be affected by the part surface status (e.g.: when placing or lifting the search unit), possibly affecting the measurement accuracy of the TOF change.

Another inconvenience of this prior art is that the sound paths from the probe to the wedge bottom can change if the wedge bottom is worn, being potentially another factor of instability.

Yet another inconvenience of this prior art is that the zone for the detection of the temperature change is not near the weld. Because the zone of the wedge bottom with which the temperature change is monitored is below the PA probe, that zone is a little bit far from the hot weld. The separation is particularly obvious for a wedge of big angle that is often used to efficiently generate shear waves in the part.

The General Electric patent U.S. Pat. No. 8,192,075 B2 discloses another method for counterworking the temperature change in wedge. According to the method, the temperature change is sensed by two separate temperature sensors, the first one is placed on the part to measure the part surface temperature and the second one is placed on top of the wedge to measure the ambient temperature. According to the patent, the temperature field in the wedge as well as the LW velocity field in the wedge can be deduced from the temperatures measured at the two above locations, and then the focal laws are modified in real time by taking into account the LW velocity field in the wedge. This method is very expensive and very complex, and for the case of water coupling, is unable to take into account the thermal energy dissipation by the coupling water.

None of the above prior art allows directly detecting the gradient of the velocity changes in the wedge caused by the temperature changes.

SUMMARY OF THE DISCLOSURE

It would be advantageous to provide a reliable means for detecting temperature change in wedges for Phased Array Ultrasound Testing (PAUT) inspections.

It would be advantageous to use the existing equipment to detect the temperature changes at a minimum extra cost or changes.

It would be also advantageous to provide a means for monitoring the gradient of the velocity change in the wedge, in order to know the seriousness of the temperature influence and to predict the tendency and direction of the temperature variation and influence.

Accordingly, the invention intends to provide a reliable and cost-effective means for detecting temperature changes in wedges used for PAUT inspection, including attaining the advantages of providing:

i) A temperature change monitoring system using embedded reflectors in the wedge front to make the signal much more stable than in prior art, using the wedge bottom as the reflector which causes the echo amplitude and TOF to be affected by possible contact with the part to inspect or by a wearing damage to the wedge bottom;

ii) The embedded reflectors do not change the normal performance of the wedge. If they are not used, the wedge behaves just like a conventional wedge;

iii) By setting the reflectors at two height positions, the gradient of the LW velocity caused by the temperature change in wedge can be estimated, and its changing tendency can be better predicted;

iv) It is a cheap and simple way for monitoring the temperature change in wedge. Except that the wedge is different, no other equipment is required. Also, since the embedded reflectors are almost invisible, the wedge looks like the same standard wedge;

v) The setup procedure is simple;

vi) It avoids the recalibrations under different temperature conditions required by some known operational procedures. Sometimes the recalibrations are useless because, despite apparent temperatures changes in the part surface or in the ambiance, the real temperature in wedge may not have changed significantly; and vii) It can avoid the complex temperature compensation and the real-time focal law modification, which are almost impractical and too expensive for such a rare event of wedge temperature change.

The invention provides a method and system of constructing a wedge for a phased-array probe suitable for monitoring the temperature changes in the wedge using the existing PA probe. The first aspect of the invention embeds small unidirectional reflectors in the damping area of the wedge that are detectable by the phased-array probe. The second aspect of the invention places the embedded reflectors at two depths in the wedge for the purpose of sensing the LW velocity change gradient affected by temperature changes in the wedge.

Other features and advantages of the present invention will become apparent from the following description of the invention which refers to the accompanying drawings.

DETAILED DESCRIPTION OF EMBODIMENTS OF THE INVENTION

Figure 1:
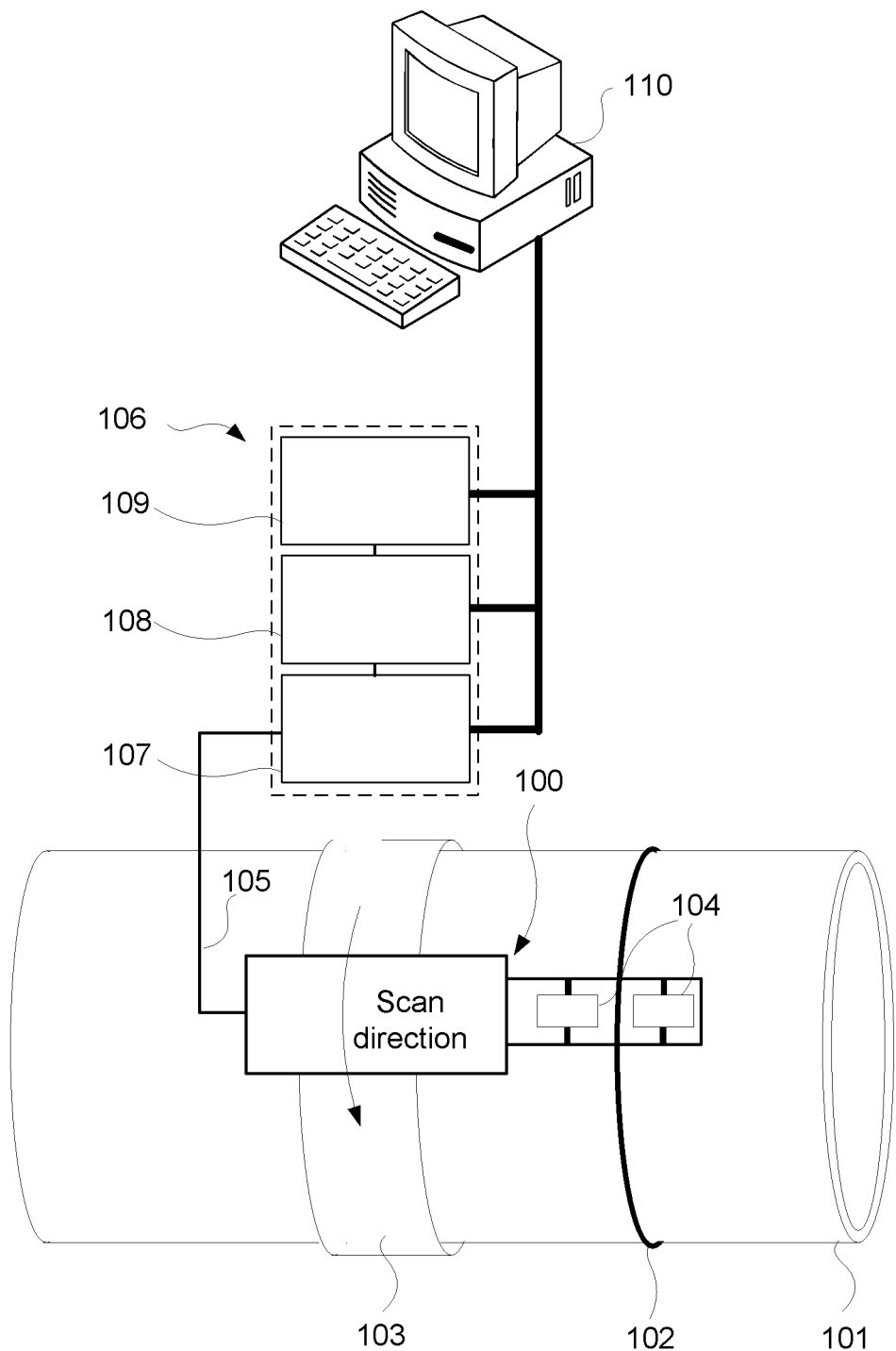
FIG. 1 is a block diagram of a girth weld inspection system with the wedge temperature change monitoring functions.
Figure 2:
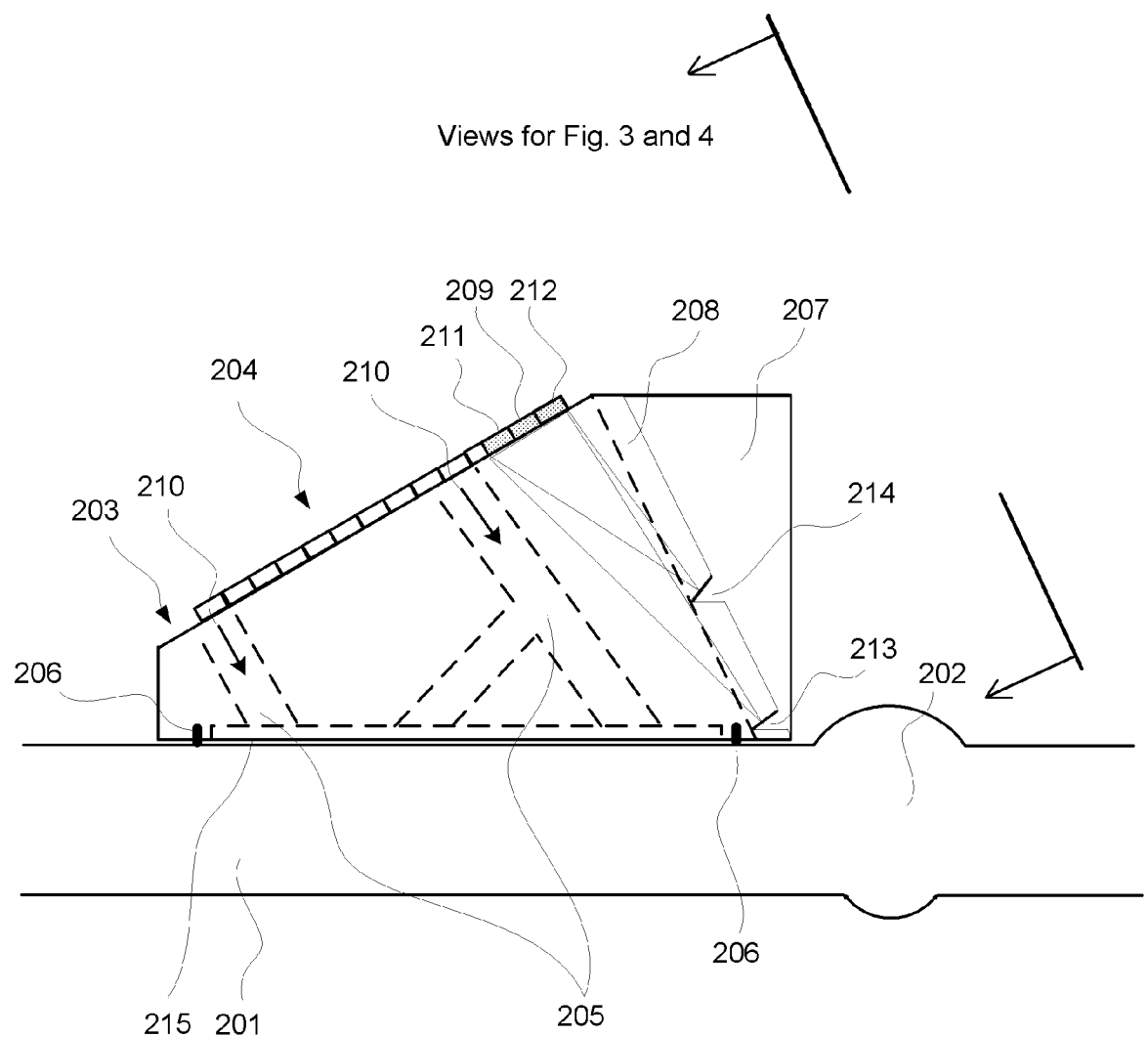
FIG. 2 is a side view of the PA probe-wedge search unit for monitoring wedge temperature changes.

Referring to FIG. 1, a scanner 100 for girth weld inspection is fixed on and guided by a weld band 103, which is secured on a pipe 101. A girth weld 102 in the pipe is to be scanned by scanner 100. Scanner 100 comprises a phased-array search unit module 104, which, for the standard configuration, includes two phased-array probe units facing each other and situated on opposed sides of girth weld 102. The signal from one PA-wedge search unit, whose generation method is shown in FIG. 2, is input into a data processing module 106, which includes three sub-modules, including: i) a temperature change detection module 107, in which the temperature change and temperature gradient are detected, ii) a temperature change warning and alarm module 108, and iii) a focal law update module 109, in which the focal laws are modified according to the velocity gradient detected in temperature change dectection module 107. These modules are controlled by a computer/processor 110.

Referring to FIG. 2, a search unit comprising a wedge 203 and a PA probe 204 is placed on the surface of a part 201, e.g., a pipe, with a weld seam 202. Weld seam 202 can be newly welded and the location where the search unit is placed still hot, but the temperature has been cooled to below 80° C. for ultrasonic coupling with water. Anti-wearing pins 206 fixed in the four corners of the bottom of the wedge allow keeping a small gap 215 of about 0.1 mm between the wedge bottom and the part surface. An irrigation network 205 of the wedge allows coupling water 210 to be pumped through the top inlets. The network of the irrigation system is so arranged in the bottom and sides of the wedge that water can not only fill up the whole wedge bottom area but can also keep the wedge body at the temperature of the water.

PA probe 204 generates beams of ultrasonic waves for weld inspection by using different apertures and focal laws (not shown in the figure). These ultrasonic beams are coupled into the wedge, and travel through gap 215 via the coupling water to reach the weld zone and, if they encounter any flaws, reflect back to PA probe 204.

When the ultrasonic beams transmit through gap 215, a portion of the ultrasonic waves skip back towards the wedge front, generating unwanted wedge echoes that need to be attenuated (the wedge echoes are not shown in the figure). To this end, in front of wedge 203 is provided a damping material zone 207, formed with grooves and serrations 208. Since the acoustic impedance of the damping material is similar to that of the wedge material, unwanted wedge echoes can be efficiently attenuated by the absorption and scattering by the combination of damping material 207 and grooves of serrations 208.

In some of grooves of serrations 208, small reflectors 213 and 214 are embedded (only two of them can be seen in this side view). These reflectors are unidirectional, i.e., they reflect the ultrasonic beams coming directly from the probe aperture and they absorb and scatter the wedge echoes coming from the bottom of the wedge.

Beam apertures 211 and 212 fire and, respectively, direct highly focused ultrasonic beams respectively to reflectors 213 and 214, and the Times of Flight (TOFs) from the apertures to the reflectors are respectively measured. The TOFs can be mainly influenced by the velocity change in the portion of the wedge body where the temperature changes. Therefore, measured values of those TOFs allow determining the LW velocity changes in the wedge that are caused by the wedge temperature changes, which is important for the weld testing process.

Still referring to FIG. 2, when beam apertures 211 and 212 and the adjacent apertures are used for the normal inspection of the part, these testing apertures can also detect reflectors 213 and 214 via beam divergence. However, because the TOFs from the reflectors are shorter than the TOFs from the interface echoes (from gap 215), the unwanted echoes from reflectors 113 and 114 do not appear in the ultrasonic image of the part being tested.

Because of the unidirectional feature of reflectors 213 and 214, the unwanted wedge echoes generated by the normal inspection beams via the beam skips from gap 215 are absorbed and scattered by the reflector bottoms, and in any case the PA probe cannot detect reflectors 213 and 214 via wedge bottom skips.

The height position of reflector 214 measured from gap 215 is so determined that its TOF to an aperture 209 is shorter than the TOF of the side lobe of the same beam to the wedge bottom. In this way, the TOF of beam aperture 212 is uniquely influenced by the TOF change caused by the temperature change in the wedge, but is not influenced by any spurious beam divergence.

The height position of reflectors 213 are near to the wedge front bottom, so that temperature changes can be sensed early and quickly. The height position of reflectors 213 are selected to cause the TOF to be later than the TOF of the LW waves travelling from aperture 209 to the wedge bottom. Normally, the height position of reflectors 213 are near the wedge bottom. Because the beam 211 is highly focused, the TOF is stable at the eventual appearance of side lobe noise of beam aperture 211 (not shown in the figure).

In practice, reflectors 213 can be used to provide a pre-alarm of temperature changes in the wedge bottom, while reflector 214 provides an alarm of temperature changes in the wedge body. Reflectors 213 and 214, located at different depths in the wedge, can also be used to estimate the temperature gradient in the wedge and predict the direction of the LW velocity changes in the wedge caused by temperature changes. The use of the reflectors at two levels can provide greater flexibility in the inspection practices. For example, it is possible that a temperature change in wedge bottom is only superficial and temporary, and so a pre-alarm is issued, but the testing need not be suspended because of that event.

For both the inspecting beams and the monitoring beams (i.e., 211 and 212), the time delays of their LW velocity changes in response to the temperature changes should be in the same order. In other words, the alarm of the temperature change in the wedge is substantially synchronized with the event of the refraction angle change in the part.

Figure 3:
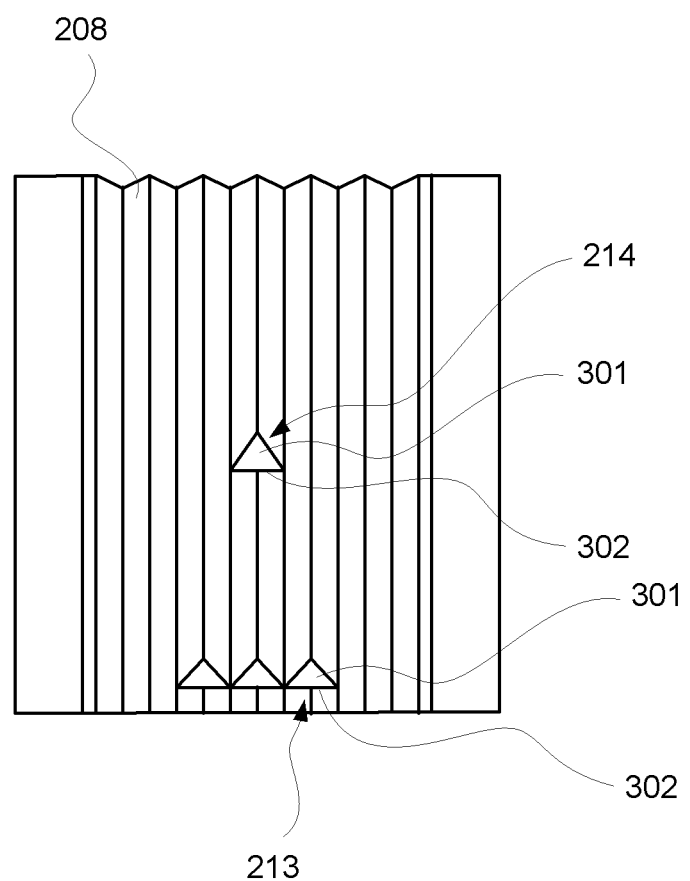
FIG. 3 is a front end view of the wedge front before the damping material injection, with the details of the unidirectional reflectors for the main embodiment illustrated.

FIG. 3 is a front end view of the wedge front before the damping material is casted. Each reflector 213 or 214, embedded in some of the grooves of serrations 208, has a top 301 and a bottom 302. Top 301 is debonded with the damping material, forming a reflective surface. The debonded surface can be achieved using surface contamination or Teflon tape isolation. In order to obtain maximum reflections, top 301 of reflectors 213 and 214 are oriented to face the nearest aperture of probe 204 and a line between the center of the nearest aperture and the center of reflectors 213 and 214's top surface is largely perpendicular to the reflectors 213 and 214's top surface. Bottom 302, whose surface is substantially parallel to gap 215, will be bonded with the damping material, forming absorbing and scattering surfaces.

Preferably, there is only one reflector 214, since a strong reflection is not required. As for reflectors 213, forming the lateral width of the reflection area, i.e., the quantity of 213 reflectors, is designed to cover the beam width at that depth. Generally speaking, the more reflectors, the higher the reflection. However, a lateral reflection area wider than the beam width cannot increase much more the reflection.

Figure 4:
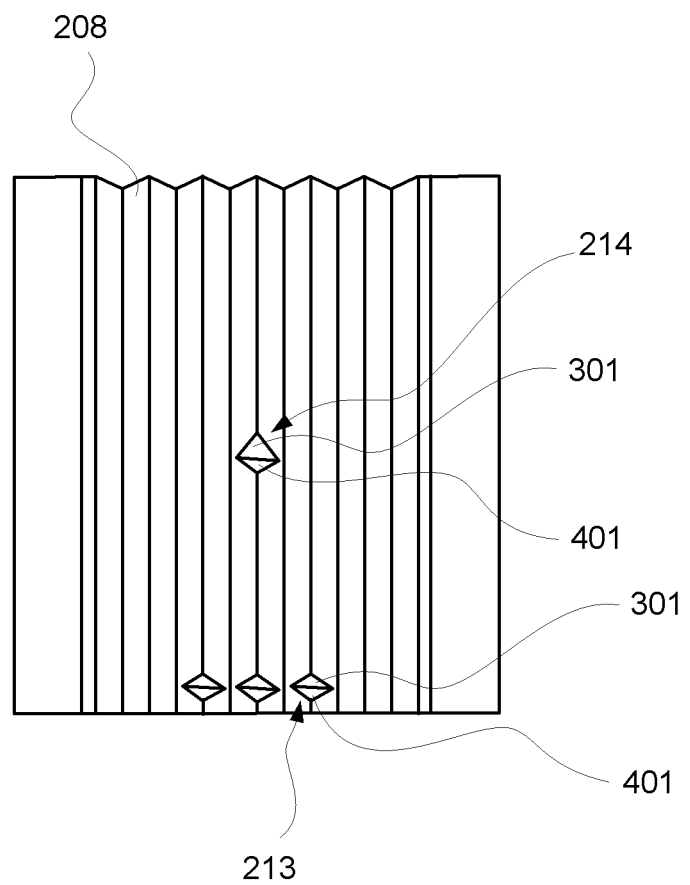
FIG. 4 shows the front end view of the wedge front before the damping material injection, including the unidirectional reflectors, according to a second embodiment.

FIG. 4 shows the front end view of the wedge front before the damping material is casted in accordance with a second embodiment. To obtain maximum reflections, top 301 of reflectors 213 and 214, embedded in some of grooves of serrations 208, are orientated to the center of nearest aperture 209, whose size is pre-determined. A bottom 401 of reflectors 213 and 214 are tilted with respect to the wedge bottom plane so that they can scatter the residual unabsorbed wedge echoes to either side of the wedge and deflect those echoes away from the beam instance plane directly under PA probe 204. This way the wedge echoes, if there are still any, can be further practically attenuated or deflected from being sensed.

Figure 5:
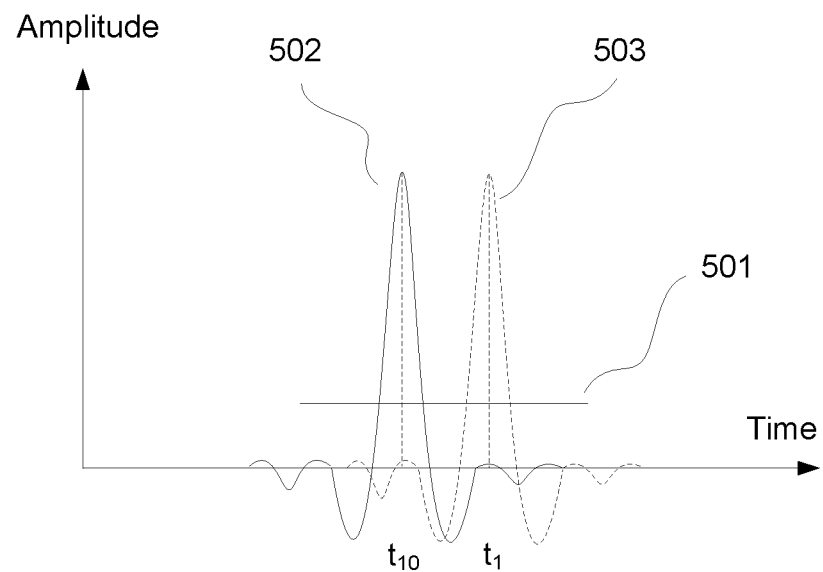
FIG. 5 illustrates measurement of the TOF difference as the wedge temperature changes.

FIG. 5 is a diagram that explains the operative function of temperature change detection module 107 in FIG. 1. Beam aperture 211 or 212 (FIG. 2) detects reflectors 213 or reflector 214 and then generates an A-scan 502 as shown in FIG. 5. Taking the detection of reflectors 213, for example, a gate 501 includes the maximum peak of A-scan 502 and its variation range. Under the normal inspection condition, i.e. with the coupling water running normally and without any direct contact between the wedge bottom and the part surface, gate 501 detects the TOF of the maximum peak at $t_{10}$ and the value thereof is saved in the acquisition unit as the reference. In case there is a temperature change in wedge, the LW velocity in wedge may be affected and A-scan 502 shifts to a position 503 with the TOF being $t_1$ as shown. The difference between $t_1$ and $t_{10}$ represents the change of temperature somewhere in the sound path from aperture 209 to reflectors 213. The difference is constantly monitored by the acquisition unit. If the difference between $t_1$ and $t_{10}$ is greater than a preset threshold, a pre-alarm is issued. The different time thresholds respectively for the detections of reflectors 213 and 214 can be determined individually by experiments. For example, a side-drill-hole in a test block is detected at the maximum refraction angle, i.e., the most sensitive angle to the temperature change in wedge, under different wedge temperatures, and the unacceptable error in the refraction angle is collated with the TOF change, i.e., the time threshold, detected with the temperature change monitoring beam apertures 211 or 212.

Figure 6:
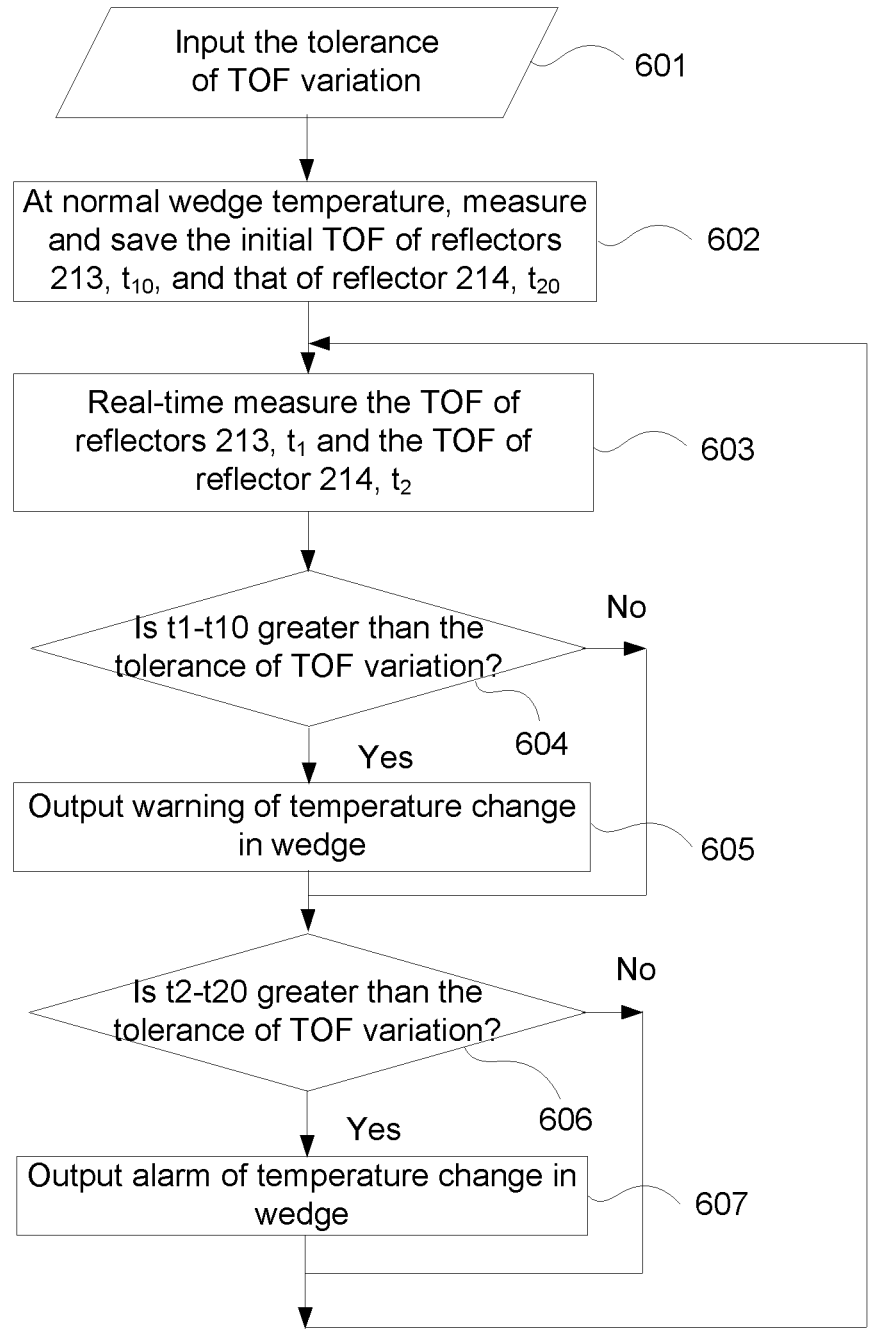
FIG. 6 is a flowchart for the module of warning and alarm of the temperature change in the wedge.

FIG. 6 shows the flowchart for the function of temperature warning and alarm module 108 in FIG. 1. In a block 601, the tolerance of TOF variation, which is for both the detection of reflectors 213 and that of reflector 214, is input. In a block 602, the initial TOF between aperture 209 and reflectors 213, $t_{10}$, and that for reflector 214, $t_{20}$, are measured (see also FIG. 5) and saved as references. In a block 603, where the loop for monitoring the temperature change in wedge begins, the TOF between aperture 209 and reflectors 213, $t_1$, and that for reflector 214, $t_2$, are measured. In a block 604, the TOF from reflectors 213, $t_1$, is compared with that measured at normal temperature, $t_{10}$, and if the difference is greater than the tolerance of TOF variation, a warning is output in a block 605. In a block 606, the TOF of reflector 214, $t_2$, is compared with that measured at normal temperature, $t_{20}$, and if the difference is greater than the tolerance of TOF variation an alarm is output in a block 607. The process loops to block 603 and repeats itself.

Figure 7:
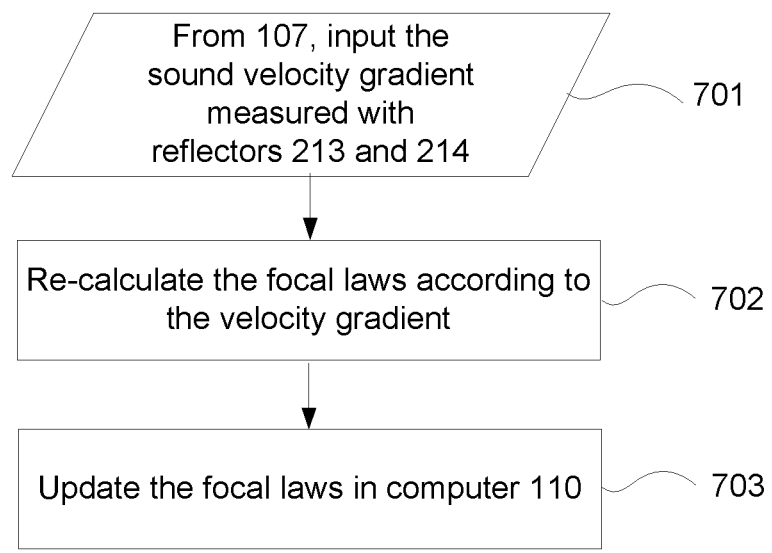
FIG. 7 is a flowchart for the module of focal law recalculation.

FIG. 7 is a flowchart for the function of focal law update module 109 in FIG. 1. In a block 701, the velocity gradient estimated by function of focal law update module 107 that takes the measurement of the TOFs respectively from reflectors 213 and 214 is input. In a block 702, the focal laws are re-calculated according to the velocity gradient. In a block 703, the updated focal laws are transmitted to computer/processor 110, which then controls the inspection with the new focal laws.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A coupling wedge, configured to be coupled with a phase array ultrasonic probe which is used with a phase array inspection system, wherein the probe, through a plurality of apertures, provides excitation waves to test a test object and receives echo waves from the test object, the wedge comprising:
   a body having a bottom side configured to face the test object, a front side generally oriented at a first angle to the bottom side and a top side generally oriented at a second angle to the bottom side and configured to couple with the apertures of the probe;
   at least one reflector formed and positioned on the front side of the wedge with a predetermined position from the bottom side of the wedge, the at least one reflector having a reflector's top surface and a reflector's bottom surface;
   wherein the reflector's top surface is oriented to face a nearest aperture of the probe and a line between substantially the center of the nearest aperture and substantially the center of the reflector's top surface is largely perpendicular to the reflector's top surface.

2. The coupling wedge of claim 1, wherein the at least one reflector comprises a plurality of reflectors.

3. The coupling wedge of claim 2, wherein the plurality of reflectors comprise at least one lower reflector located nearer to the bottom side of the coupling wedge and at least one upper reflector located further away from the bottom side of the coupling wedge and closer to the apertures.

4. The coupling wedge of claim 3, wherein the at least one lower reflector comprises a plurality of lower reflectors wherein measurements of time of flights (TOF) from the upper and lower reflectors located at at least two different levels in the wedge are used to deduce a temperature gradient in the front side of the wedge.

5. The coupling wedge of claim 4, wherein at least several of the plurality of reflectors each has a respective reflector's top surface and a respective reflector's bottom surface.

6. The coupling wedge of claim 5, wherein the bottom surface is substantially parallel to the bottom side of the coupling wedge.

7. The coupling wedge of claim 5, wherein the bottom surface is tilted with respect to a bottom plane of the bottom side of the coupling wedge in a configuration that effectuates the deflection of residual echoes in the wedge to either side of the beam incidence plane.

8. The coupling wedge of claim 1, including a conduit within the coupling wedge for conducting couplant fluid through the body of the coupling wedge and into a gap located between the bottom side of the coupling wedge and the test object.

9. The coupling wedge of claim 8, including grooves fabricated on the front side of the wedge.

10. The coupling wedge of claim 1, including a damping material applied to the front side of the coupling wedge to dampen undesired, spurious echo waves from the object.

11. The coupling wedge of claim 10, wherein the damping material has an acoustic impedance which matches that of the body of the coupling wedge.

12. The wedge of claim 1, wherein time of flight (TOF) values of the waves from the at least one reflector to one of the apertures is used to deduce a change of temperature in the wedge.

13. A phased array inspection system configured to be operable with a phase array ultrasonic probe and a coupling wedge, wherein the probe, having a plurality of apertures, provides excitation waves to test a test object and receives echo waves from the test object, and the probe and the system is configured to be operable with the coupling wedge of claim 1; and wherein the wedge having a bottom side configured to face the test object, a front side generally oriented at a first angle to the bottom side and a top side generally oriented at a second angle to the bottom side and configured to couple with the apertures of the probe, and the wedge further having at least one reflector formed and positioned on the front side of the wedge with a predetermined position from the bottom side of the wedge; and wherein the at least one reflector has a top surface which is oriented to face a center of a nearest aperture of the wedge;
   the system comprising,
   a data acquisition unit,
   a data processing module for analyzing the signals corresponding to the echo waves, the data processing module further comprising a temperature detection module which detects a temperature change based on time of flight (TOF) values of the waves from the at least one reflector to at least one of the apertures.

14. The system of claim 13, further including an alarm module for issuing an alarm indicating that the change of temperature of the wedge is outside an acceptable range.

15. The system of claim 13, further including a module for altering focal laws associated with the acquisition unit to compensate for temperature changes detected in the wedge based on times of flight of echo signals from the at least one reflector.

16. The system of claim 13, wherein the at least one reflector comprises a plurality of reflectors located nearer the bottom side of the coupling wedge and at least one reflector located comparatively further away from the bottom side of the coupling wedge and closer to the apertures.

17. The system of claim 16, wherein the reflectors have a bottom surface which is substantially parallel to the bottom face and the bottom side of the coupling wedge.

18. A method of inspecting a test object using a phased array inspection system configured to be operable with a phase array ultrasonic probe, wherein the probe, having a plurality of apertures, provides excitation waves to inspect the test object and receives echo waves from the test object, the method comprising the steps of:
   i) providing a wedge having a body with a bottom side configured to face the object, a front side generally oriented at an angle to the bottom side and a top side coupled with the probe, and at least one reflector formed and positioned on the wedge front side with a predetermined distance from the bottom side of the wedge; wherein the reflector's top surface is oriented to face a nearest aperture of the probe and a line between substantially the center of the nearest aperture and substantially the center of the reflector's top surface is largely perpendicular to the reflector's top surface
   ii) coupling the probe with the system,
   iii) coupling the probe with the wedge, and coupling the wedge with the test object,
   iv) generating waves and measuring Time-of-flight (TOF) values of the waves from one of the plurality of apertures to the reflector;
   v) determining a change in the temperature of the wedge based on the TOF values.

19. The method of claim 18, including altering focal laws in the system to compensate for temperature variations in the wedge which are outside a permitted temperature range.

20. The method of claim 18, including outputting an alarm indicative of a temperature variation in the coupling wedge that is outside a permitted temperature range.

* * * * *